(12) United States Patent
Kushida

(10) Patent No.: US 6,213,959 B1
(45) Date of Patent: Apr. 10, 2001

(54) MORPHOMETRIC MODELING SYSTEM AND METHOD

(76) Inventor: Clete Kushida, 101 E. Middlefield Rd. #8, Mountain View, CA (US) 94043-3865

( * ) Notice: Subject to any disclaimer, the term of this patent is extended or adjusted under 35 U.S.C. 154(b) by 0 days.

(21) Appl. No.: 09/467,403

(22) Filed: Dec. 20, 1999

Related U.S. Application Data

(63) Continuation of application No. 09/061,020, filed on Apr. 15, 1998, now Pat. No. 6,048,322.

(51) Int. Cl.$^7$ .................................................. A61B 5/103
(52) U.S. Cl. ............................ 600/587; 600/590; 33/514; 433/72
(58) Field of Search .................................... 600/587, 590; 33/511, 512, 513, 514, 495, 500, 424, 471; 433/2, 68, 72, 75

(56) References Cited

U.S. PATENT DOCUMENTS

| 766,562 | 8/1904 | Wertz | 33/150 |
|---|---|---|---|
| 3,634,942 | 1/1972 | Nicyper | 33/150 |
| 3,740,779 | 6/1973 | Rubricuis | 25/4 |
| 3,745,665 | 7/1973 | Shilliday | 33/174 D |
| 4,226,025 | 10/1980 | Wheeler | 600/587 |
| 4,979,519 | 12/1990 | Chavarria et al. | 600/590 |
| 5,158,096 | 10/1992 | Clark et al. | 128/777 |
| 5,226,428 | 7/1993 | Lee | 600/590 |
| 5,361,506 | 11/1994 | Beeuwkes, III | 600/590 |
| 5,376,093 | 12/1994 | Newman | 600/587 |
| 5,381,799 | 1/1995 | Hamilton et al. | 600/590 |
| 5,678,317 | 10/1997 | Stefanakos | 600/587 |

FOREIGN PATENT DOCUMENTS

| 4111278A | 4/1991 | (DE) . |
|---|---|---|
| 850896 | 12/1939 | (FR) . |

OTHER PUBLICATIONS

Kushida, Clete A., "A Predictive Morphometric Model for the Obstructive Sleep Apnea Syndrome," Ann Intern Med. (1997), vol. 127, pp 581–587.

Primary Examiner—Cary O'Connor
Assistant Examiner—Charles Marmor, II
(74) Attorney, Agent, or Firm—Michael W. Haas

(57) ABSTRACT

A tool for measuring the oral cavity. The tool includes a first measuring member having a first leg portion and a dial portion with graduations provided thereon and a second measuring member having a second leg portion and a pointer. The pointer moves across the dial upon pivotal movement of measuring members such that the pointer designates one of the graduations to indicate the spacing between the leg portions. Second graduations provided on one of the measuring members are indicative of a second measured value. The tool also includes a support member positionable in the oral cavity of a patient with the patient biting down on the upper and lower bite surfaces of the support. The support includes an opening shaped to slidably receive and support the first leg portion and a slot offset from the opening. The slot is shaped to slidably receive the second leg portion as the second measuring member is pivoted relative to the first measuring member.

7 Claims, 4 Drawing Sheets

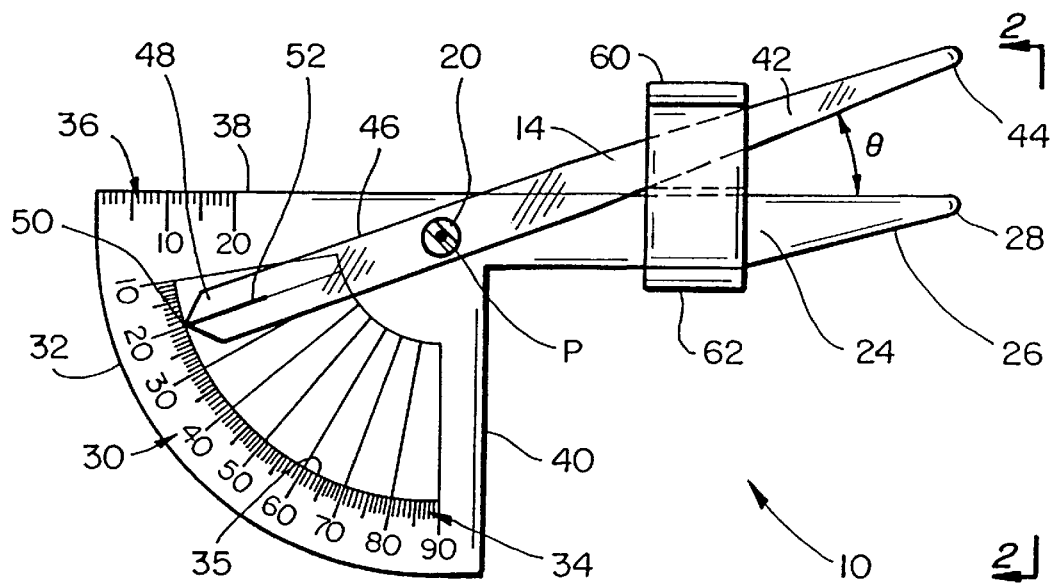
FIG_1
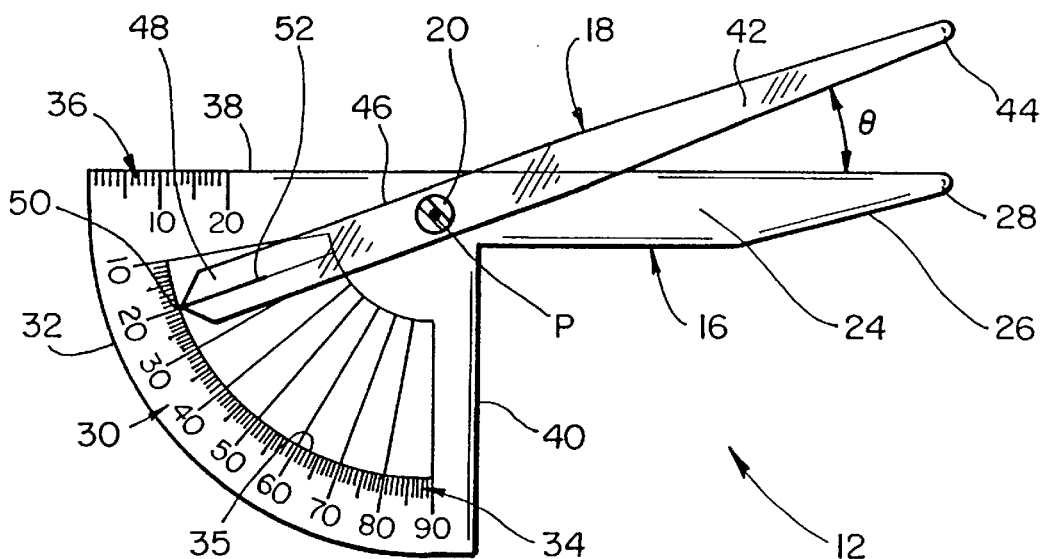
FIG_3

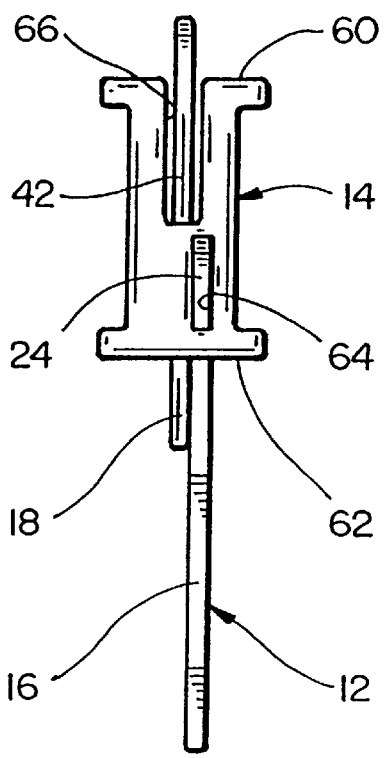
FIG_2
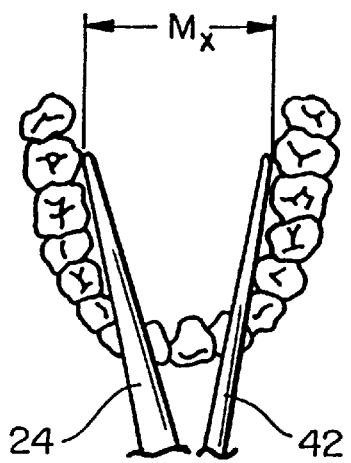
FIG_5
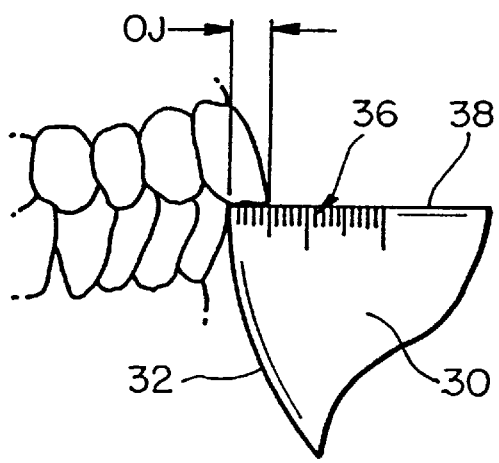
FIG_6

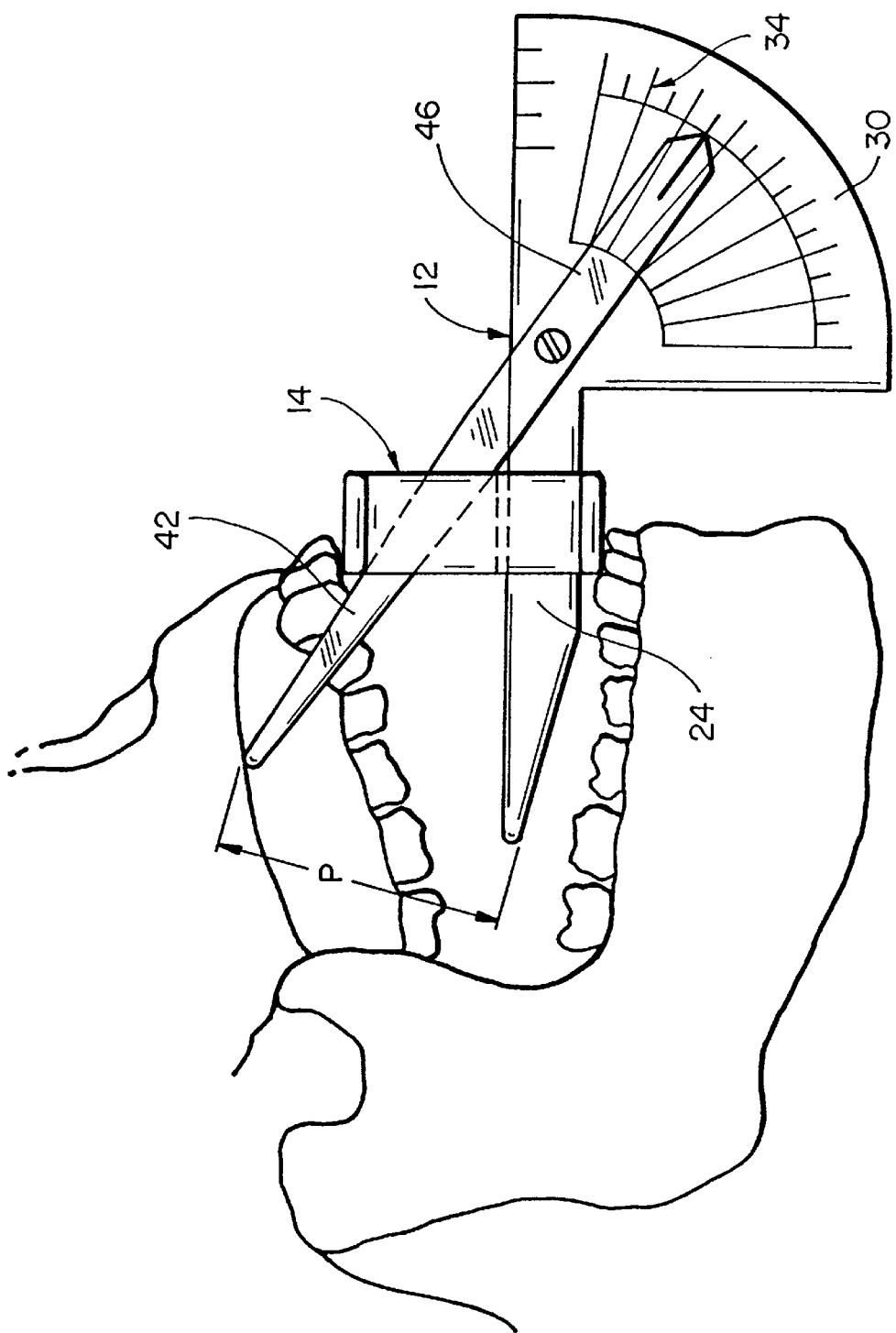
FIG_4

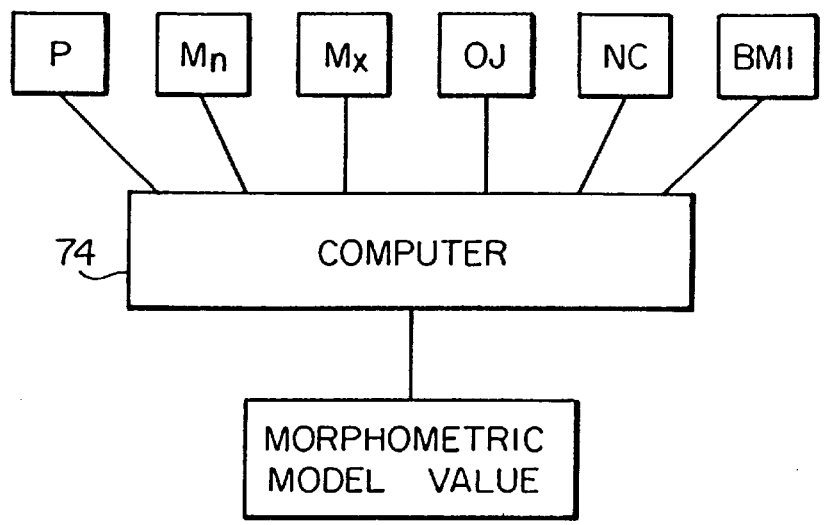
FIG_7
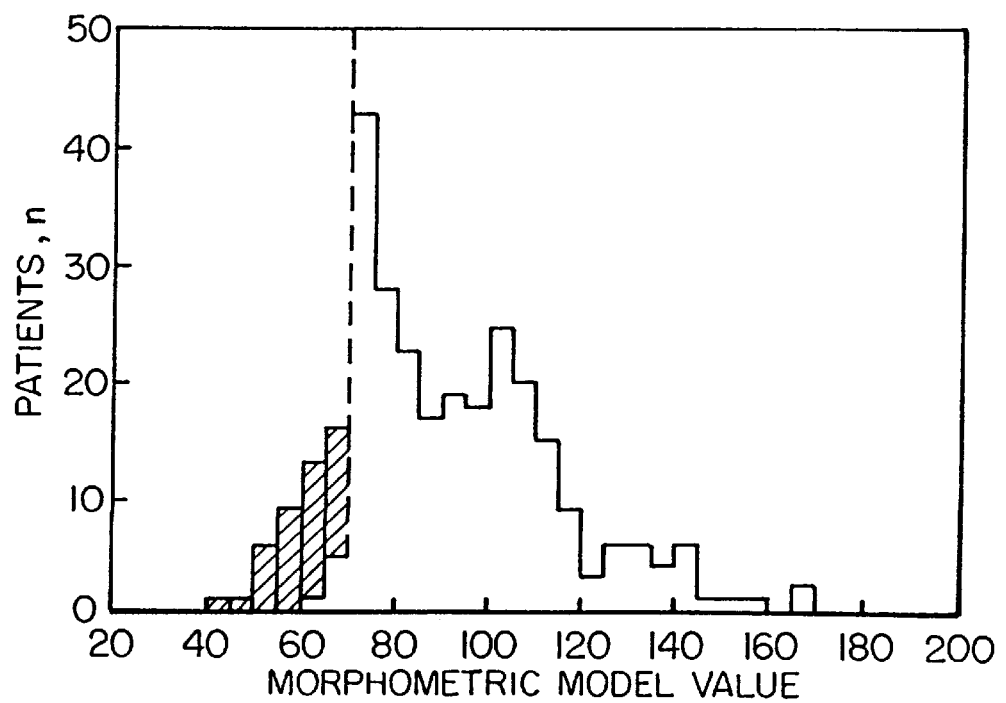
FIG_8

MORPHOMETRIC MODELING SYSTEM AND METHOD

This application is a continuation of U.S. Ser. No. 09/061,020 filed Apr. 15, 1998, now U.S. Pat. No. 6,048,322.

BRIEF DESCRIPTION OF THE INVENTION

The present invention relates in general to the preliminary screening for a sleep-related breathing disorder and, more particularly, to a tool for use in obtaining measurements of the oral cavity.

BACKGROUND OF THE INVENTION

The obstructive sleep apnea syndrome (OSAS) is a sleep disorder in which the patient exhibits breathing pauses during sleep, resulting in excessive daytime sleepiness, sleep fragmentation, and intermittent hypoxia. Patients suffering from the disorder have a greater risk of developing diurnal hypertension, myocardial infarction, ventricular failure, pulmonary hypertension, cardiac dysrhythmias and stroke. In addition to health problems, OSAS significantly reduces the effectiveness and alertness of the individual during the day which adversely effects the individual's lifestyle and increases the risk of injury to the individual and others from motor vehicle and work-related accidents.

OSAS is typically diagnosed by polysomnographic testing. This procedure involves monitoring the patient overnight to record brain activity, eye movements, chin and leg muscle movements, cardiac rhythm, snoring intensity, oronasal airflow, respiratory muscle effort, and blood oxygen saturation. The test is time consuming, labor intensive and expensive. Thus, a method of screening patients to reliably determine whether or not they may be at risk for OSAS reduces the number of patients who are unnecessarily subjected to polysomnographic testing. More importantly, earlier diagnosis and treatment of OSAS would be promoted because the screening results would eliminate the reluctance of a physician to prescribe polysomnographic testing for those patients who do not exhibit dramatic OSAS symptoms.

Mathematical formulas have been developed to clinically predict whether a patient is likely to suffer from OSAS. These mathematical models primarily rely on measurements of body mass index and neck circumference, two factors which are indicative of the obesity of the patient. Obesity is one of the important risk factors for OSAS. However, not all patients who suffer from OSAS are obese. Although prior mathematical models have combined the body mass index and neck circumference measurements with oxygen saturation levels, witnessed apneas and questionnaire data, these mathematical models are of little use in screening patients who are not obese. A system of screening patients without relying on whether or not they are obese would ensure that further testing is prescribed for all patients at risk for OSAS independent of their body weight.

Another significant risk factor in the development of OSAS is craniofacial dysmorphism (disproportionate craniofacial anatomy). Abnormalities associated with craniofacial dysmorphism include a reduction in the upper airway caliber which makes the airway susceptible to collapse during sleep. Abnormalities in craniomandibular morphology, such as a narrow or posteriorly displaced mandible, are often found in OSAS patients. Another abnormality commonly found in OSAS patients is a highly arched palate. A system of quickly and accurately detecting the presence of a narrow or posteriorly displaced mandible and/or a highly arched palate would facilitate the assessment of a patient's OSAS risk.

OBJECTS AND SUMMARY OF THE INVENTION

It is a primary object of the present invention to provide a system of screening patients for OSAS.

It is a further object of the present invention to provide a tool which may be used to measure the oral cavity of a patient.

It is another object of the present invention to provide a measurement tool which may be used to easily, accurately and quickly obtain measurements of the palatal height, the spacing between the second molars, and the overlap between the upper and lower incisors.

It is yet another object of the present invention to provide a system for converting measurements of the oral cavity and other patient data into a morphometric model value which may be used to predict whether further testing of the patient for OSAS is warranted.

A more general object of the present invention is to provide a measurement tool which may be efficiently and inexpensively manufactured, and which is suitable for either disposal after a single use or sterilization to permit the tool to be reused.

In summary, the present invention provides a tool for measuring the oral cavity. The tool includes first and second measuring members pivotally coupled together for relative pivotal movement of the measuring members about a pivot axis. The first measuring member includes a first leg portion positioned forwardly of the pivot axis and a dial portion with graduations provided thereon. The second measuring member includes a second leg portion positioned forwardly of the pivot axis and a pointer. The second leg portion moves relative to the first leg portion and the pointer moves across the dial upon relative pivotal movement of the first and second measuring members to designate the first graduations and indicates a first measured value indicative of the spacing between the leg portions. One of the measuring members also has second graduations provided thereon in the form of a linear scale such that the second graduations provide a measurement indicative of the spacing between two members, for example the size of the overlap between the upper and lower right central incisors. The measurement tool also includes a support member positionable in the oral cavity of a patient, with the patient biting on upper and lower bite surfaces of the support member. The support member is formed with an opening shaped to slidably receive and support the first leg portion and a slot offset from the opening. The slot is shaped to receive the second leg portion, with the second leg portion being movable within the slot as the second measuring member is pivoted relative to the first measuring member.

Additional objects and features of the invention will be more readily apparent from the following detailed description and appended claims when taken in conjunction with the drawings.

BRIEF DESCRIPTION OF THE DRAWINGS

FIG. 1 is a front plan view of a measurement tool in accordance with the present invention, shown with the tool in an open position.

FIG. 2 is an enlarged end view taken substantially along line 2—2 in FIG. 1.

FIG. 3 is a front plan view of the measurement device of the tool of FIG. 1.

FIG. 4 is a schematic view of the measurement tool of FIG. 1, shown measuring the palatial height of the oral cavity.

FIG. 5 is a schematic view of the measurement tool of FIG. 1, shown measuring the distance between the left and right molars.

FIG. 6 is a schematic view of the measurement tool of FIG. 1, shown measuring the overlap of the upper and lower incisors.

FIG. 7 is a diagram of the processing system of the present invention.

FIG. 8 is graphical depiction of the number of patients per morphometric model number.

DETAILED DESCRIPTION OF THE INVENTION

Reference will now be made in detail to the preferred embodiment of the invention, which is illustrated in the accompanying figures. Turning now to the drawings, wherein like components are designated by like reference numerals throughout the various figures, attention is directed to FIGS. 1–3.

Tool 10, constructed in accordance with the present invention, is particularly suitable for quickly and accurately measuring the oral cavity of a patient. In general, the tool 10 includes a measurement device 12 and a support member 14 which cooperates with the measurement device 12 as shown particularly in FIGS. 1 and 2 and described in more detail below. As shown particularly in FIGS. 1 and 3, the measurement device 12 includes a pair of measuring members 16 and 18 which are pivotally coupled together at pivot axis P. The measuring members 16 and 18 may be coupled together by any suitable pivot or fastener 20 which permits relative pivotal movement of the two members 16 and 18. In the illustrated embodiment, a screw and anchor nut are used to secure the measuring members 16, 18 together, although it is to be understood that other suitable fasteners may also be employed. In this embodiment, the interior diameters of the holes (not shown) formed through the measuring members are greater than the maximum exterior diameter of the fastener 20 so that the pivoting of the measuring members is not significantly restricted by friction. However, in other embodiments of the invention the relative sizes of the pivot and the holes formed through the measuring members 16, 18 may be selected so that the measuring members 16, 18 are substantially held in place by friction until a positive force is applied to one of the members. The frictional forces would hold the measuring members 16, 18 in position, allowing the device 12 to be handled for reading and recording the measurement without unintentional movement of the measuring members 16, 18. Bushings, bearings or other devices may also be employed if desired, although such devices would increase the complexity of the device 12 and the cost of manufacture.

The first measuring member 16 has a leg portion 24 positioned forwardly of the pivot axis P. The leg portion 24 includes a tapered front end 26 which accommodates the profile of the relaxed tongue and facilitates insertion of the leg portion 24 into the support member 14 as described below. The narrow tip 28 of the front end 26 also facilitates use of the device 12 as a caliper to measure the distance between the second molars on the left and light sides of the oral cavity. The measuring member 16 also includes a dial portion 30. In the illustrated embodiment, outer edge 32 of the dial portion 30 has an arcuate shape since the measuring member 18 travels in a circular path. However, it is to be understood that the dial portion may also have other shapes within the scope of this invention. The arcuate extent of the dial portion 30 is about 90°, but may be increased or decreased to meet the needs of a particular application. A series of graduations, generally designated 34, are provided on the dial portion 30. The graduations 34 may be etched into the dial portion 30, printed on the dial portion or applied using other suitable means.

In the illustrated embodiment, the graduations identify the angle θ between the measuring members 16, 18. The dial portion 30 may also include graduations in which the angular measurement has been converted into a measurement of the linear distance between the tip 28 and the front end of the measuring member 18, allowing the height or width measured using the device 12 to be immediately identified without further calculation. If desired, the graduations may designate both the angles and the converted linear measurement.

The measuring member 16 also includes a second series of graduations, generally designated 36. The graduations 36 provide a linear scale which may be used to measure the spacing between two members, such as the overlap between the upper and lower right central incisors. In the illustrated embodiment, the graduations 36 are provided along the straight edge 38 of the dial portion, extending inwardly from the outer edge 32 such that the outer edge may be positioned directly against the lower right central incisor. The curvature of the outer edge 32 accommodates the profile of the gums of the lower central incisors and the lower lip. It is to be understood that the graduations may also be positioned in other locations on the measuring member 16 such as along the inner edge 40 of the dial portion. Although not shown, the graduations 36 may also be provided on the second measuring member 18 instead of member 16. The graduations 36 may be applied using printing, etching or other suitable techniques.

The second measuring member 18 includes a leg portion 42 positioned forwardly of the pivot axis P. The leg portion 42 is of substantially the same length as the leg portion 24. The leg portions 24, 42 each have a length of about 70 mm to 80 mm, for example 75 mm. The leg portion 42 is tapered to a narrow tip 44 which is substantially centered on the central axis of the measuring member 18.

The member 18 includes a pointer portion 46 spaced from the leg portion 42. The pointer portion 46 has a pointed end 48, the apex 50 of which coincides with the central axis of the measuring member. The apex 50 moves along the graduated curve 35 and designates one of the graduations 34 to indicate the angle θ between the leg portions 24 and 42. The pointer 46, which is transparent, is provided with a line 52 extending inwardly from the apex 50 along the central axis of the member 18 to facilitate the identification of which of the graduations 34 is designated by the pointer 46. It is to be understood that the pointer portion 46 may have other configurations suitable for pointing to one of graduations 34. For example, the length of the pointer portion 46 may be increased such that the line 52 extends across the graduated curve to provide the primary means of reading the designated graduation. With this modification, where the apex 50 is not used to identify the designated graduation, the end of the pointer portion 46 may be blunt, curved to follow the arcuate edge 32 of the dial portion 30, or have other shapes.

The support member 14 is shown in FIGS. 1 and 2. One function of the support member 14 is to provide a biting block which is inserted between the upper and lower jaws of the patient and used to hold the jaws in a partially open position. This is to standardize the jaw opening across patients, which coincides with a 20 degree angle (not shown) between the tips of the upper and lower central incisors with the axis of the angle at the mandibular condyle. The support member 14 includes upper and lower bite surfaces 60 and 62 which are contacted by the patient's upper and lower central incisors, respectively, when the support member 14 is clamped between the upper and lower jaws. The support member 14 is positioned so that upper and lower bite surfaces 60 and 62 are parallel to the horizontal plane of the upper surfaces of the teeth on the lower jaw. In the illustrated embodiment, the bite surfaces 60, 62 have a width greater than the width of the body of the support member 14 to maximize the surface area of the bite surfaces 60, 62 while still allowing visualization of the oral cavity and reducing the amount of material required to form the support member 14, thereby reducing the cost of manufacture. However, it is to be understood that the upper and lower bite surfaces 60, 62 may be coextensive with the remainder of the support member 14 if desired. The bite surfaces 60, 62 have a width of about 15 mm to 25 mm, for example 21 mm, although in other modifications of the invention the width of the bite surfaces 60, 62 may be larger or smaller. The height of the support member 14 is about 35 mm to 45 mm, for example 40 mm, opening the mouth a sufficient amount to measure the palate height with the device 12. However, it is to be understood that the height of the support member 14 may be decreased to measure the oral cavity of children, for example.

Another function of the support member 14 is to support the measuring members 16, 18 so that a reliable and accurate measurement of the palate height may be obtained. The support member includes a bore 64 formed through the support member 12. The bore 64 is shaped to slidably receive the leg portion 24 of the first measuring member 16 and support the leg portion 24 in position during the measurement. The tapered front end 26 of the leg portion 24 facilitates insertion of the leg portion 24 into the bore 64. In the illustrated embodiment, the bore 64 follows the shape of the exterior of the leg portion and is slightly larger than the leg portion 24 such that the leg portion 24 may be easily slid into place, but vertical and side-to-side movement of the leg portion 24 within the bore 64 is limited. However, it is to be understood that the size of the bore 64 relative to the leg portion 24 may be increased provided the bore 64 continues to support the device 12 in the proper position.

The support member 14 also includes a slot 66 shaped to slidably receive the leg portion 42 of the second measuring member 18. Slot 66 is also used to align support member 14 between the upper and lower jaws. Support member 14 is positioned so that slot 66 is aligned with the grooves between the two central incisors of the upper and lower jaws. As shown particularly in FIG. 2, the slot 66 is positioned vertically above the bore 64, and the central axis of the slot is offset from the central axis of the bore 64. Since the position of the device 12 within the support member 14 is controlled by the bore 64, the slot 66 is substantially wider than the leg portion 42 such that the leg portion 42 may move without contacting the side walls of the slot 66. With this configuration, the variations in the size of the leg portion 42 or the exact position of the leg portion 42 relative to the measuring member 16 can be accommodated. However, it is to be understood that the size of the slot 66 may be increased or decreased within the scope of this invention.

The device 12 and support member 14 are formed of a material which is suitable for insertion into the oral cavity of the patient, such as plastic or acrylic. In the preferred embodiment, the second measuring member is transparent such that the graduations 34 on the dial portion 30 may be viewed through the pointer portion 46. The first measuring member may also be transparent.

FIGS. 4–6 show the use of the tool 10 of this invention to measure the oral cavity. FIG. 4 shows the measurement of the palatal height (P), or the distance between the dorsum of the tongue at the median lingual sulcus to the highest point of the palate. In FIG. 4, the support member 14 is gripped between the upper and lower jaws. The leg portion 24 of the measuring member 16 is passed through the bore 64 and rests on the tongue (not shown). As the leg portion 24 of the measuring member 16 is advanced forward in bore 64, the measuring member 18, with the leg portion 42 positioned in the slot 66, is automatically pivoted clockwise relative to the measuring member 16 until the pointed end 44 of the leg portion contacts the palate. This occurs because, as measuring member 16 advances forward in bore 64, the leg portion 42 of measuring member 18 slides along the lower edge of slot 66, resulting in an increase in angle θ. The size of the opening between the leg portions 24 and 42, in the form of angle θ or the linear distance between the pointed end 44 and the tip 28, is indicated by the pointer portion 46 which designates the appropriate one of the graduations 34. The value associated with the designated graduation, which represents the palatal height P, is noted.

FIG. 5 shows the measurement device 12 measuring the width of the mandible. As shown in FIG. 5, the spacing between the mesial surfaces of the crowns of the second molars is measured to determine the mandibular intermolar distance (Mn), and the process is repeated with the upper jaw to determine the maxillary intermolar distance (Mx). These measurements are obtained by inserting the leg portions 24, 42 of the device 12 into the oral cavity and positioning the tip 28 on one of the second molars and the end 44 on the opposite second molar. The distance separating the tip 28 and end 44, in the form of the angle θ between the leg portions 24, 42 or the linear distance between the tip and end, is determined by reading the graduation on the dial portion 30 which is identified by the pointer portion 46.

FIG. 6 shows the tool 10 measuring the overjet or overlap between the upper and lower incisors (OJ). Specifically, the horizontal overlap of the crowns of the upper and lower right central incisors is measured. This measurement is obtained by positioning the second graduations 36 adjacent to the overlap. With the device 12 of the present embodiment, where the graduations 36 are positioned on the edge 38 of the measuring member 16, the outer edge 32 of the dial portion 30 is positioned against the surface of the lower right central incisor and the graduation 36 located adjacent to the tip of the upper right central incisor is noted.

Once these data are obtained, the morphometric model value (MMV) for the patient is obtained using the following formula:

$$MMV = [P + (Mx - Mn) + 3OJ] + 3[\text{Max}(BMI - 25, 0)]\frac{NC}{BMI}$$

where:
  P: palatal height in millimeters (FIG. 4)
  Mx: maxillary intermolar distance in millimeters (FIG. 5)
  Mn: mandibular intermolar distance in millimeters (FIG. 5)
  OJ: incisor overjet in millimeters (FIG. 6)

NC: neck circumference in centimeters, measured at the level of the cricothyroid membrane BMI: body mass index, defined as weight in kilograms divided by the square of height in meters.

In addition to the oral cavity measurements P, Mx, Mn and OJ, enclosed within the first set of brackets for illustrative purposes, the above formula also incorporates data indicative of the patient's obesity if the body mass index is greater than 25 kg/m². As discussed above, obesity is an important risk factor for the development of OSAS. If a patient is not obese, for the purposes of this analysis the body mass index is no greater than 25, craniofacial dysmorphism is the sole factor for determining the patient's risk for OSAS. Using this system as a basis for screening patients prior to prescribing further testing, the amount of craniofacial dysmorphism which must be present to signal that further testing is needed varies independently from whether a patient is obese or not.

If the patient is not obese (i.e., BMI≦25), the second half of the formula automatically becomes zero, and the equation reduces to the first half of the formula:

$$MMV = P + (Mx - Mn) + 3OJ$$

The remaining formula indicates OSAS risk based only on the degree of craniofacial dysmorphism since the patient is not obese. Thus, the formula can be used for screening all patients for OSAS, including those whom are obese, not obese, and those with or without craniofacial dysmorphism.

As is diagrammatically illustrated in FIG. 7, a computer 74 (e.g., programmed calculator, software program) is preferably used to compute the model value number. The user inputs the necessary data, in the preferred embodiment the palatal height P, maxillary intermolar distance Mx, mandibular intermolar distance Mn, the incisor ovedjet OJ, the neck circumference NC, and the body mass index BMI. With the tool 10 of the illustrated embodiment, the graduations 34 identify the angle between the leg portions 24, 42 in degrees. Computer 74 is configured to receive the values for P, Mx and Mn in degrees and convert these values into a linear distance using stored information on the measurement device 12. As discussed above, in other modifications of the invention the graduations may identify the values for P, Mx and Mn in millimeters, in which case the computer 74 would be configured to receive the linear measurements and calculate the morphometric model value therefrom. The computer 74 produces an output indicating the morphometric model value for the patient. The computer 74 may be programmed to compare the calculated morphometric model value with the target value and indicate when the calculated value is equal to or greater than the target value such that further testing is required. Alternatively, the user may personally evaluate the calculated model number and the need for further testing for OSAS.

EXPERIMENTAL DATA

Three hundred patients underwent traditional testing by polysomnography to determine whether they had OSAS. These patients were also evaluated using measurements equivalent to those obtained from morphometric measurement tool 10 and system of the present invention, with the first equation being used to calculate the morphometric model value. The results are summarized in the following table.

| CHARACTERISTIC | PATIENTS WITH OSAS | PATIENTS WITHOUT OSAS |
| --- | --- | --- |
| Men/women | 203/51 | 21/25 |
| Age (y) | 48.1 ± 12.4 | 40.2 ± 14.0 |

| CHARACTERISTIC | PATIENTS WITH OSAS | PATIENTS WITHOUT OSAS |
| --- | --- | --- |
| Epworth Sleepiness Scale score | 11.5 ± 5.7 | 7.5 ± 5.9 |
| Weight (kg) | 101.9 ± 25.8 | 68.7 ± 9.9 |
| Height (cm) | 174.3 ± 9.4 | 171.8 ± 8.7 |
| Body Mass Index (kg/m²) | 33.6 ± 8.5 | 23.2 ± 2.6 |
| Neck Circumference (cm) | 41.7 ± 4.7 | 34.5 ± 3.4 |
| Maxillary Intermolar Distance (mm) | 42.0 ± 3.6 | 39.8 ± 3.8 |
| Mandibular Intermolar Distance (mm) | 39.8 ± 3.8 | 37.8 ± 3.4 |
| Palatal Height (mm) | 52.4 ± 4.1 | 48.0 ± 4.4 |
| Overjet (mm) | 3.9 ± 2.0 | 3.3 ± 1.5 |
| Respiratory Disturbance Index (events/h) | 40.7 ± 42.8 | 0.8 ± 0.8 |
| Minimum Oxygen Saturation (%) | 79.5 ± 12.7 | 95.1 ± 3.0 |
| Morphometric Model Value | 95.3 ± 21.2 | 61.6 ± 6.2 |

In general, patients with morphometric model values of 70 or more had OSAS, while patients with values less than 70 did not exhibit evidence of OSAS. Thus, a target value of 70 was selected. FIG. 8 shows the number of patients having each morphometric value, with the hatched areas representing the non-OSAS group. As shown in FIG. 8, a smaller number of patients with a model number of less than 70, six total, had OSAS. The model value of the majority of these patients was between 65 and 70. Thus, patients with model values between 65 and 70 should not be automatically dismissed as being without OSAS solely on the basis of their model value. Instead, other factors such as the patient's symptoms and known sleep problems as well as questionnaire data should be considered and a subjective determination made of whether further testing is necessary. Further, the practitioners subjective opinion that the patient may have OSAS should not be completely ignored for patients with a model value of less than 65.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the Claims appended hereto and their equivalents.

What is claimed is:

1. A morphometric modeling system comprising:
   (a) anatomical feature measuring means for determining first anatomical data of a patient including:
      a first measurement value indicative of a distance between a highest point of the palate in an oral cavity of the patient and a tongue, a second measurement value indicative of an overlap of the upper and lower right central incisors, a third measurement value indicative of a distance between a molar on the right side of the upper jaw and a molar on the left side of the upper jaw, and a fourth measured value indicative of a distance between a molar on the right side of the lower jaw and a molar on the left side of the lower jaw; and (b) processing means for determining a morphometric model value for such a patient based on the first anatomical data, said morphometric model value being indicative of a likelihood that such a patient suffers from obstructive sleep apnea syndrome.

2. The system of claim 1, wherein the anatomical feature measuring means includes a tool comprising:

first and second measuring members pivotally coupled together for relative pivotal movement of said first and said second measuring members about a pivot axis;

said first measuring member including a first leg portion positioned forwardly of said pivot axis and a dial portion having graduations provided thereon extending rearwardly of said pivot axis;

said second measuring member including a second leg portion positioned forwardly of said pivot axis and a pointer extending rearwardly of said pivot axis, said second leg portion being pivotal relative to said first leg portion, and said pointer moving across said dial upon pivotal movement of said first and said second leg portions such that said pointer designates one of said graduations to indicate a measured value indicative of the spacing between said first and said second leg portions; and a support member positionable in the oral cavity of a patient, said support member having upper and lower bite surfaces, an opening shaped to slidably receive and support said first leg portion and a slot offset from said opening, said slot being shaped to slidably receive and support said second leg portion to pivot said second measuring member relative to said first measuring member as said first and said second leg portions are moved into said opening and said slot, respectively.

3. The system of claim 2, wherein one of said first and said second measuring members on said tool further includes first graduations provided thereon in the form of a linear scale.

4. The system of claim 1, wherein the anatomical feature measuring means includes a tool comprising:

first and second measuring members pivotally coupled together for relative pivotal movement of said first and said second measuring members about a pivot axis;

said first measuring member including a first leg portion positioned forwardly of said pivot axis and a dial portion rearwardly of said pivot axis having first graduations provided thereon;

said second measuring member including a second leg portion positioned forwardly of said pivot axis and a pointer extending rearwardly of said pivot axis, said second leg portion moving relative to said first leg portion and said pointer moving across said dial upon pivotal movement of said second measuring member relative to said first measuring member such that when said first and said second measuring members are held stationary with said leg portions in an open position, said pointer designates one of said first graduations to indicate a first measured value; and one of said first and said second measuring members having second graduations provided thereon on the rearwardly extending portion, said second graduations being indicative of a second measured value.

5. The system of claim 1, further comprising means for determining second anatomical data of such a patient including a body mass index and a neck circumference, and wherein said processing means is configured to receive said second anatomical data and to determine said morphometric model valve for such a patient based on said first anatomical data and said second anatomical data.

6. A morphometric modeling method comprising the steps of:

(a) determining first anatomical data of a patient including:

a first measurement value indicative of a distance between a highest point of the palate in an patient's oral cavity of the patient and a tongue, a second measurement value indicative of an overlap of the upper and lower right central incisors, a third measurement value indicative of a distance between a molar on the right side of the upper jaw and a molar on the left side of the upper jaw, and a fourth measured value indicative of a distance between a molar on the right side of the lower jaw and a molar on the left side of the lower jaw; and (b) processing the first anatomical data to determine a morphometric model value for such a patient based thereon, said morphometric model value being indicative of a likelihood that such a patient suffers from obstructive sleep apnea syndrome.

7. The method of claim 6, further comprising determining second anatomical data for such a patient including a body mass index and a neck circumference, and wherein the processing step includes determining said morphometric model of such a patient based on said first anatomical data and said second anatomical data.

* * * * *